United States Patent [19]
Grinstaff et al.

[11] Patent Number: 5,880,149
[45] Date of Patent: Mar. 9, 1999

[54] METAL COMPLEXES AS CYSTEINE PROTEASE INHIBITORS

[75] Inventors: Mark W. Grinstaff, Durham, N.C.; Harry B. Gray, Pasadena; Thomas J. Meade, Altadena, both of Calif.

[73] Assignee: California Institute of Technology, Pasadena, Calif.

[21] Appl. No.: 721,872

[22] Filed: Sep. 27, 1996

Related U.S. Application Data

[60] Provisional application No. 60/004,451 Aug. 28, 1995.
[51] Int. Cl.$^6$ .......................... A61K 31/28; C07H 23/00; C07F 1/08
[52] U.S. Cl. .......................... 514/492; 514/495; 514/499; 514/501; 536/17.1; 536/22.1; 536/23.1; 556/113; 556/114; 556/116; 556/117
[58] Field of Search ..................................... 556/113, 114, 556/116, 117; 514/492, 495, 499, 501; 536/17.1, 22.1, 23.1

[56] References Cited

PUBLICATIONS

Chakraborty, H. et al., "Catalytic Activities of Schiff Base Aquocomplexes of Copper(ii) in the Hydrolysis of Amino Esters," *Chemical Abstracts*, 122(7):1154, abstract: 81932t (1995).

Vol'pin, M.E. et al., "Transition Metal Complexes as Catalysts in Biochemical Systems. Interaction with Electron Transfer Processes," *Chemical Abstracts*, 95:212, abstract: 182415f (1981).

Wu, Z. et al., "Synthesis of Chelates of 2–HOC$_4$H$_4$(CHNCH$_2$CH$_2$OH) with Cobalt(II), Nickel(II), Copper(II) and Primary Tests of Their Anticancer Activities," *Chemical Abstracts*, 107(6):749, abstract: 50768e (1987).

Hu, V.W. et al., "X–Ray Absorption Edge Studies on Oxidized and Reduced Cytochrome c Oxidase," *Chemical Abstracts*, 87(23):235–236, abstract: 179854c (1987).

DeFilippo, D. et al., "Silver and Gold(I) Complexes with Thiomorpholin–3–One. Kinetics of Reduction of Gold(III)," 75(6):315, abstract:40913e (1971).

Sun Bai, K and D.L. Leussing, "Kinetics of Formation of N–Salicylideneglycinatonickel(II), –Copper(II) and – Zinc(II). Elucidation of the Template Mechanism," *Journal of the American Chemical Society*, 89(24):6126–6130 (1967).

Roeper, J., et al., "Square–Planar Copper(II) Chelate Complexes of the ONN,X Type (X–Monodentate Ligand): Kinetics of Ligand Substitution as Studied in Acetone and the Effect of Water," *Chemcical Abstracts*, 111(2):660, abstract: 16690w (1989).

Becker, M. et al., "Kinetics of Ligand Substitution in Platinum(II) Complexes: A Study on the Concept of Nucleophillic Discrimination," *Chemical Abstracts*, 105(22):750, abstract: 202128v (1966).

Elo, H. et al., "Antiproliferative Activity of Derivatives of Trans–bis(Salicyladoximato Copper (II) in Vitro. Some In Vivo Properties of the Parent Compound," *Chemical Abstracts*, 108(13):24, abstract: 106022x (1968).

Elo, H. et al., "Reaction of the Antiproliferative and Antineoplastic Agent Trans–Bis(Salicylaldoximato) Copper(II) and Related Chelates with Glutathione and Cysteine. Corelation Between Reactivity and Biological Activity," 107(18):918, abstract: 167735h (1987).

Meade et al., U.S. Ser. No. 08/571,364, filed Dec. 12, 1995, entitled "Cobalt Schiff Base Compounds".

Meade et al., U.S. Ser. No. 08/570,761, filed Dec. 12, 1995, entitled "Cobalt Schiff Base Compounds".

Meade et al., U.S. Ser. No. 08/358,068, filed Dec. 14, 1994, entitled "Water Soluble CO(II) Schiff's Base Compounds".

Doraswamy et al., Indian Journal of Chemistry, vol. 15A, No. 2, pp. 129–131, Feb. 1977.

Jani et al., Indian Journal of Chemistry, vol. 15A, No. 8, pp. 750–752, Aug. 1977.

Patel et al., Indian Journal of Chemistry, vol. 20A, No. 6, pp. 628–629, Jun. 1981.

Roper et al., Inorganic Chemistry, vol. 28, No. 12, pp. 2323–2329, Jun. 1989.

Costes et al., Inorganica Chimica Acta, vol. 237, Nos. 1–2, pp. 57–63, Sep. 1995.

*Primary Examiner*—Porfirio Nazario-Gonzalez
*Attorney, Agent, or Firm*—Flehr Hohbach Test Albritton & Herbert LLP; Richard F. Trecartin; Robin M. Silva

[57] ABSTRACT

The invention relates to metal complexes used to bind proteins and enzymes.

13 Claims, No Drawings

METAL COMPLEXES AS CYSTEINE PROTEASE INHIBITORS

This application claims the benefit of U.S. Provisional application No. 60/004,451 filed 28 Sep. 1995.

FIELD OF THE INVENTION

The invention relates to metal complexes used to bind proteins and enzymes.

BACKGROUND OF THE INVENTION

The area of inorganic pharmaceuticals is in its infancy. The most common and well studied inorganic pharmaceutical is cis-platinum, an anticancer drug (Lippard, Science 218:1075–1082 (1982); Rosenberg, Nature 222:385 (1969); Cleare et al., Bioinorg. Chem. 2:187 (1973)). This inorganic pharmaceutical is clinically used to treat a variety of cancers. The mode of action of cis-platinum is believed to be by interacting with DNA to prevent the cell from proliferating.

Three gold compounds have also been investigated and clinically used to treat arthritis (Dash Metal Ions Biol. Systm. 14:179 (1982); Elder et al., Chem. Rev. 87:1027 (1987)). These include Auranofin, a gold sodium thiomalate and a gold thioglucose compound, depicted below:

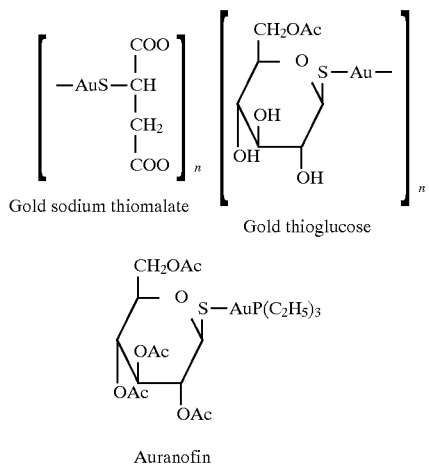

Gold sodium thiomalate

Gold thioglucose

Auranofin

The current understanding on the therapeutic action of gold compounds to treat arthritis is limited. The mode of action of anti-arthritic gold drugs is largely unknown, but it may involve binding of Au(I) to protein thiol groups, thus inhibiting the formation of disulfide bonds, and could lead to denaturation and subsequent formation of macroglobulins. See Bioinorganic Chemistry (Eds Bertini, Gray, Lippard, and Valentine, pg 519, 1994).

A class of cobalt (III) schiff-base compounds have been reported to have antivirial, antitumor, and antimicrobial activities, as well as antiinflammatory properties (see U.S. Pat. Nos. 4,866,054; 4,866,053; 5,049,577; 5,106,841; 5,142,076; and 5,210,096).

SUMMARY OF THE INVENTION

The present invention provides metal complexes having the formula:

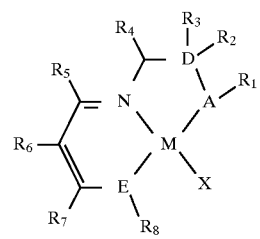

wherein
M is a transition metal ion selected from the group consisting of Cu, Ag, Au, Ni, Pd and Pt;
A is either nitrogen or oxygen;
E is oxygen, sulfur, nitrogen or selenium;
D is carbon, boron or phosphorus;
X is a counterion or a neutral coordinating ligand;
$R_1$ is hydrogen, halogen, alkyl, alkyl alcohol, alcohol, alkyl thiol, alkyl acid, alkyl amine, amine, aryl, a targeting moiety, or may be absent when A is oxygen, sulfur or selenium;
$R_2$ is hydrogen, halogen, alkyl, alkyl alcohol, alcohol, alkyl thiol, alkyl acid, alkyl amine, amine, aryl, a targeting moiety, carbonyl oxygen, phosphonyl oxygen, or —$OR_5$ when A is boron;
$R_3$ is hydrogen, halogen, alkyl, alkyl alcohol, alcohol, alkyl thiol, alkyl acid, alkyl amine, amine, aryl, a targeting moiety, —$OR_5$ when A is boron or phosphorus, or is absent when $R_2$ is carbonyl oxygen;
$R_4$ is hydrogen, halogen, alkyl, alkyl alcohol, alcohol, alkyl thiol, alkyl acid, alkyl amine, amine, aryl, or a targeting moiety;
$R_5$ is hydrogen, halogen, alkyl, alkyl alcohol, alcohol, alkyl thiol, alkyl acid, alkyl amine, amine, aryl, or a targeting moiety;
$R_6$ is hydrogen, halogen, alkyl, alkyl alcohol, alcohol, alkyl thiol, alkyl acid, alkyl amine, amine, aryl, a targeting moiety, or, together with $R_7$, may form a cycloalkyl or aryl group;
$R_7$ is hydrogen, halogen, alkyl, alkyl alcohol, alcohol, alkyl thiol, alkyl acid, alkyl amine, amine, aryl, a targeting moiety, or, together with $R_6$, may form a cycloalkyl or aryl group; and
$R_8$ is hydrogen, halogen, alkyl, alkyl alcohol, alcohol, alkyl thiol, alkyl acid, alkyl amine, amine, aryl, a targeting moiety, or may be absent when E is oxygen, sulfur or selenium.

Further provided are metal complexes having the formula:

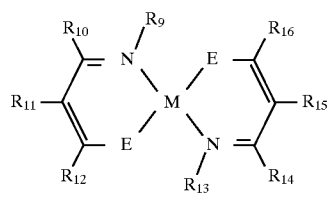

wherein
M is a transition metal ion selected from the group consisting of Cu, Ag, Au, Ni, Pd and Pt;
E is oxygen, sulfur, or selenium;
$R_9$ is hydrogen, halogen, alkyl, alkyl alcohol, alcohol, alkyl thiol, alkyl acid, alkyl amine, amine, aryl, or a targeting moiety;

$R_{10}$ is hydrogen, halogen, alkyl, alkyl alcohol, alcohol, alkyl thiol, alkyl acid, alkyl amine, amine, aryl, or a targeting moiety;

$R_{11}$ is hydrogen, halogen, alkyl, alkyl alcohol, alcohol, alkyl thiol, alkyl acid, alkyl amine, amine, aryl, a targeting moiety, or, together with $R_{12}$, may form a cycloalkyl or aryl group;

$R_{12}$ is hydrogen, halogen, alkyl, alkyl alcohol, alcohol, alkyl thiol, alkyl acid, alkyl amine, amine, aryl, a targeting moiety, or, together with $R_{11}$, may form a cycloalkyl or aryl group;

$R_{13}$ is hydrogen, halogen, alkyl, alkyl alcohol, alcohol, alkyl thiol, alkyl acid, alkyl amine, amine, aryl, or a targeting moiety;

$R_{14}$ is hydrogen, halogen, alkyl, alkyl alcohol, alcohol, alkyl thiol, alkyl acid, alkyl amine, amine, aryl, or a targeting moiety;

$R_{15}$ is hydrogen, halogen, alkyl, alkyl alcohol, alcohol, alkyl thiol, alkyl acid, alkyl amine, amine, aryl, a targeting moiety, or, together with $R_{16}$, may form a cycloalkyl or aryl group; and $R_{16}$ is hydrogen, halogen, alkyl, alkyl alcohol, alcohol, alkyl thiol, alkyl acid, alkyl amine, amine, aryl, a targeting moiety, or, together with $R_{15}$, may form a cycloalkyl or aryl group.

Also provided are metal complexes having the formula:

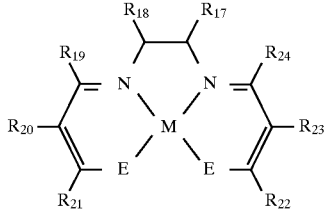

wherein

M is a transition metal ion selected from the group consisting of Cu, Ag, Au, Ni, Pd and Pt;

E is oxygen, sulfur, or selenium;

$R_{17}$ is hydrogen, halogen, alkyl, alkyl alcohol, alcohol, alkyl thiol, alkyl acid, alkyl amine, amine, aryl, or a targeting moiety;

$R_{18}$ is hydrogen, halogen, alkyl, alkyl alcohol, alcohol, alkyl thiol, alkyl acid, alkyl amine, amine, aryl, or a targeting moiety;

$R_{19}$ is hydrogen, halogen, alkyl, alkyl alcohol, alcohol, alkyl thiol, alkyl acid, alkyl amine, amine, aryl, or a targeting moiety;

$R_{20}$ is hydrogen, halogen, alkyl, alkyl alcohol, alcohol, alkyl thiol, alkyl acid, alkyl amine, amine, aryl, a targeting moiety, or, together with $R_{21}$, may form a cycloalkyl or aryl group;

$R_{21}$ is hydrogen, halogen, alkyl, alkyl alcohol, alcohol, alkyl thiol, alkyl acid, alkyl amine, amine, aryl, a targeting moiety, or, together with $R_{20}$, may form a cycloalkyl or aryl group;

$R_{22}$ is hydrogen, halogen, alkyl, alkyl alcohol, alcohol, alkyl thiol, alkyl acid, alkyl amine, amine, aryl, a targeting moiety, or, together with $R_{23}$, may form a cycloalkyl or aryl group;

$R_{23}$ is hydrogen, halogen, alkyl, alkyl alcohol, alcohol, alkyl thiol, alkyl acid, alkyl amine, amine, aryl, a targeting moiety, or, together with $R_{22}$, may form a cycloalkyl or aryl group; and $R_{24}$ is hydrogen, halogen, alkyl, alkyl alcohol, alcohol, alkyl thiol, alkyl acid, alkyl amine, amine, aryl, or a targeting moiety.

DETAILED DESCRIPTION OF THE INVENTION

As is described below, the present invention is directed to metal compounds that can exchange or bind functional moieties such as cysteine on a protein's surface (e.g. in the active site of an enzyme) resulting in the inactivation of a biological activity of the protein due to the complexing of the functional moiety to the metal compound.

Without being bound by theory, the metal complex compounds of the present invention derive their biological activity by the substitution or addition of ligands to the metal complexes. The biological activity of the complexes results from the binding of a new ligand, most preferably the sulfur atom of the side chain of cysteine. Presumably the amino acid serving as the new ligand of the metal complex is required by the target protein for its biological activity. Thus, as is more fully described below, proteins such as cysteine proteases that utilize a cysteine in the active site, or proteins that use cysteines, for example, to bind essential metal ions, can be inactivated by the binding of the cysteine as a ligand of the metal complex, thus preventing the cysteine from participating in its normal biological function.

Accordingly, the addition of the metal complexes depicted herein are added to a protein or enzyme, for example, and one or more of the original ligands are replaced by one or more ligands from the protein. This will occur either when the affinity of the protein axial ligand is higher for the metal complex as compared to the original ligand, or when the new axial ligand is present in elevated concentrations such that the equilibrium of ligand binding favors the binding of the new ligand from the protein. This latter possibility may be encouraged by the use of a targeting moiety, which increases the presence of the metal complex at the relevant site within the target protein or enzyme.

Alternative mechanisms of inhibition include the possibility that the metal complex oxidizes the free cysteines to form a disulfide bond in the active site. The enzyme remains inhibited until the disulfide bond is reduced, returning the activity. Thus, the possibility exists that the metal complexes depicted herein may be reversible inhibitors.

Alternatively, the metal complex may oxidize the free cysteine to cysteinic acid, or acts as a catalyst with oxygen present to produce reactive species such as hydrogen peroxide, which may serve to inactivate the biological activity of the target protein.

Of particular interest are complexes of transition metals such as gold, nickel, palladium, platinum and copper, as these metals have a strong propensity to bind sulfur preferentially to other elements such as oxygen, nitrogen and carbon. Consequently these complexes will preferentially bind to the sulfur atom of a cysteine residue than serine, aspartic acid or histidine. However, while the examples and disclosure herein particularly describe this cysteine embodiment, any "reactive amino acid" may serve as the new ligand. A "reactive amino acid" is one which is capable of binding to the metal compounds of the invention as a new ligand. Thus, while the sulfur atom of the side chain of cysteine is particularly preferred, alternative embodiments utilize the nitrogen atom of the imidazole side chain of histidine, the nitrogen atom of the aromatic indole side chain of tryptophan, the sulfur atom of the side chain of methionine, the amino groups of arginine, lysine, asparagine or glutamine as the moieties which may become axial ligands as outlined above. The availability of these moieties may depend on the pH of the solution containing the protein or enzyme, since in the protonated state many of these moieties are not good electron donors suitable as ligands.

Cysteine proteases are a family of proteases that bear a thiol group at the active site. Cysteine proteases are characterized by the ability to cleave amide bonds using a synergistic interaction between a specific cysteine and histidine in the protease active site. The mechanism of amide bond cleavage is shown below.

known as dipeptidyl peptidase I), interleukin converting enzyme (ICE), calcium-activated neutral proteases, calpain I and II; viral cysteine proteases such as picornian 2A and 3C, aphthovirus endopeptidase, cardiovirus endopeptidase, comovirus endopeptidase, potyvirus endopeptidases I and II, adenovirus endopeptidase, the two endopeptidases from chestnut blight virus, togavirus cysteine endopeptidase, as well as cysteine proteases of the polio and rhinoviruses; and cysteine proteases known to be essential for parasite lifecycles, such as the proteases from species of Plasmodia, Entamoeba, Onchocera, Trypansoma, Leishmania, Haemonchus, Dictyostelium, Therileria, and Schistosoma,

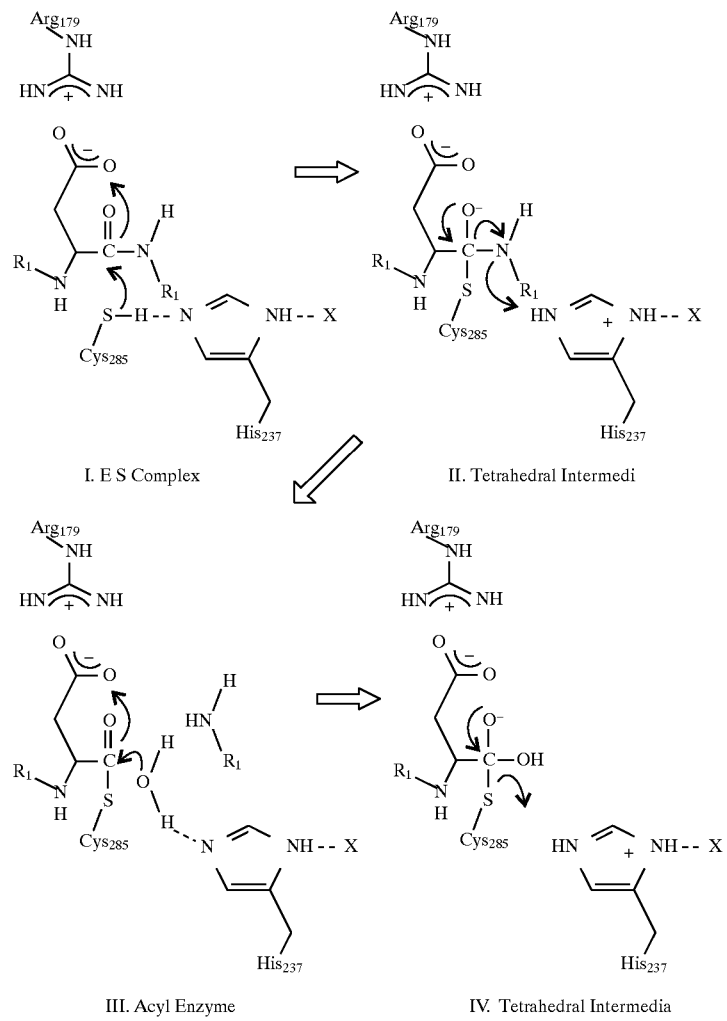

I. E S Complex

II. Tetrahedral Intermedi

III. Acyl Enzyme

IV. Tetrahedral Intermedia

Briefly stated, nucleophilic attack at the carbonyl site by the thiol group (i.e., cys) occurs first. A tetrahedral intermediate is formed which then collapses to release the amine fragment. The His then catalyzes the attack of water on the thiol ester to produce the carboxylate fragment.

These proteases are found in bacteria, viruses, eukaryotic microorganisms, plants, and animals. Cysteine proteases may be generally classified as belonging to one of four or more distinct superfamilies. Examples of cysteine proteases that may be inhibited by the novel cysteine protease inhibitors of the present invention include, but are not limited to, the plant cysteine proteases such as papain, ficin, aleurain, oryzain and actinidain; mammalian cysteine proteases such as cathepsins B, H, J, L, N, S, T and C, (cathepsin C is also such as those associated with malaria (P. falciparium), trypanosomes (T. cruzi, the enzyme is also known as cruzain or cruzipain), murine P. vinckei, and the C. elegans cysteine protease. For an extensive listing of cysteine proteases that may be inhibited by the cysteine protease inhibitors of the present invention, see Rawlings et al., Biochem. J. 290:205–218 (1993), hereby expressly incorporated by reference.

Accordingly, inhibitors of cysteine proteases are useful in a wide variety of applications. For example, the inhibitors of the present invention are used to quantify the amount of cysteine protease present in a sample, and thus are used in assays and diagnostic kits for the quantification of cysteine proteases in blood, lymph, saliva, or other tissue samples, in addition to bacterial, fungal, plant, yeast, viral or mammalian cell cultures. Thus in a preferred embodiment, the sample is assayed using a standard protease substrate. A cysteine protease inhibitor is added, and allowed to bind to any cysteine protease present. The protease assay is then rerun, and the loss of activity is correlated to cysteine protease activity using techniques well known to those skilled in the art.

The cysteine protease inhibitors are also useful to remove or inhibit contaminating cysteine proteases in a sample. For example, the cysteine protease inhibitors of the present invention are added to samples where proteolytic degradation by contaminating cysteine proteases is undesirable. Alternatively, the cysteine protease inhibitors of the present invention may be bound to a chromatographic support, using techniques well known in the art, to form an affinity chromatography column. A sample containing an undesirable cysteine protease is run through the column to remove the protease.

In a preferred embodiment, the cysteine protease inhibitors are useful for inhibiting cysteine proteases implicated in a number of diseases, as cysteine proteases have been implicated in a number of medically relevant diseases (see for example, Hook et al., FASEB J. 8:1269 (1994)). In particular, cathepsins B, L, and S, cruzain, and interleukin 1β converting enzyme are inhibited. These enzymes are examples of lysosomal cysteine proteases implicated in a wide spectrum of diseases characterized by tissue degradation. Such diseases include, but are not limited to, arthritis, muscular dystrophy, inflammation, tumor invasion, glomerulonephritis, parasite-borne infections, Alzheimer's disease, periodontal disease, and cancer metastasis. For example, mammalian lysosomal thiol proteases play an important role in intracellular degradation of proteins and possibly in the activation of some peptide hormones. Enzymes similar to cathepsins B and L are released from tumors and may be involved in tumor metastasis. Cathepsin L is present in diseased human synovial fluid and transformed tissues. Similarly, the release of cathepsin B and other lysosomal proteases from polymorphonuclear granulocytes and macrophages is observed in trauma and inflammation.

The cysteine protease inhibitors also find application in a multitude of other diseases, including, but not limited to, gingivitis, malaria, leishimaniasis, filariasis, and other bacterial and parasite-borne infections. The compounds also offer application in viral diseases, based on the approach of inhibiting proteases necessary for viral replication. For example, many picornoviruses including poliovirus, foot and mouth disease virus, and rhinovirus encode for cysteine proteases that are essential for cleavage of viral polyproteins.

Additionally, these compounds offer application in disorders involving interleukin-1β converting enzyme (ICE), a cysteine protease responsible for processing interleukin 1β. ICE is a 60 kDa tetrameric enzyme composed of two sets of two distinct subunits, a 20 kDa (p20) and 10 kDa (p10) subunit fragment. The crystal structure of ICE was recently reported (Walker et al., Cell 78:343–352 (1994); Wilson et al., Nature 370:270–275 (1994)). The active site of ICE is contains Cys285 and His237 that are responsible for its catalytic activity. ICE is very specific to its substrates and cleavage sites (Howard et al., J. Immunol. 147:2964–2969 (1991), preferring binding an aspartic acid in the $P_1$ position of the enzyme). The biological function of ICE is to specifically cleave the 33 kDa precursor protein (pIL-1β) to produce the 17 kDa inflammatory cytokine, IL-1β. This carboxy-terminated IL-1β cytokine is biologically active and can be found in the serum and synovial fluid of septic shock, rheumatoid arthritic, and diabetic patients.

The cytokine IL-1 performs a pivotal role in rheumatoid arthritis (RA) (Arend et al., Arthritis Rheum. 38:151–160 (1995); Arend et al., Arthritis Rheum. 33:305–315 (1990); Dinarello et al., N. Eng. J. Med. 328:106–113 (1993)). The IL-1 agonists, IL-1α and IL-1β are well characterized and share only minimal sequence homology (March et al., Nature 315:641–645 (1985); Gray et al., J. Immunol. 137:3644–3648 (1986)). However, the membrane bound form IL-1α and soluble IL-1β form are both known to have similar biological activity and interact with the same cellular receptors (Dower et al., Nature 324:266–268 (1986); Sims et al., PNAS U.S.A. 90: 6155–6159 (1993)). A number of strategies for blocking IL-1 have been proposed (Fanslow, 1990, Science 248:739–742; Gershenwald 1990, PNAS 87:4966–4970; Seckinger 1987, J. Immunol. 139:1546–1549; and Arend, Adv. Immunol. 54:167–227 (1993) including inhibition of ICE (Cerretti et al, J. Bacteriology 134:1141–1156 (1992); Thornberry 1992, Nature 356:768–774) and Ku et al., 1996, Cytokine 8:377–386.

Thus, for example, the cysteine protease inhibitors of the present invention may be useful in the treatment of inflammation and immune based disorders of the lung, airways, central nervous system and surrounding membranes, eyes, ears, joints, bones, connective tissues, cardiovascular system including the pericardium, gastrointestinal and urogenital systems, the skin and the mucosal membranes. These conditions include infectious diseases where active infection exists at any body site, such as meningitis and salpingitis; complications of infections including septic shock, disseminated intravascular coagulation, and/or adult respiratory distress syndrome; acute or chronic inflammation due to antigen, antibody and/or complement deposition; inflammatory conditions including arthritis, chalangitis, colitis, encephalitis, endocarditis, glomerulonephritis, hepatitis, myocarditis, pancreatitis, pericarditis, reperfusion injury and vasculitis. Immune-based diseases include but are not limited to conditions involving T-cells and/or macrophages such as acute and delayed hypersensitivity, graft rejection, and graft-versus-host disease; auto-immune diseases including Type I diabetes mellitus and multiple sclerosis. Bone and cartilage reabsorption as well as diseases resulting in excessive deposition of extracellular matrix such as interstitial pulmonary fibrosis, cirrhosis, systemic sclerosis, and keloid formation may also be treated with the inhibitors of the present invention. The inhibitors may also be useful in the treatment of certain tumors that produce IL 1 as an autocrine growth factor and in preventing the cachexia associated with certain tumors. Apoptosis and cell death are also associated with ICE (Yuan et at., Cell 75:641–652 (1993) and may be treated with the inhibitors of the present invention.

The present invention provides several classes of metal complexes which serve as cysteine protease inhibitors. Structure 1 generically depicts the first of such classes:

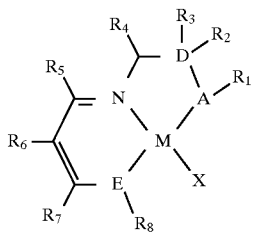

Structure 1

In this embodiment, M is a transition metal ion, A is either nitrogen or oxygen, E is oxygen, sulfur, nitrogen or selenium and D is carbon, boron (B) or phosphorus (P). X is either a counter-ion or a neutral coordinating ligand. $R_1$ is hydrogen, halogen, alkyl, alkyl alcohol, alcohol, alkyl thiol, alkyl acid, alkyl amine, amine, aryl, a targeting moiety, or may be absent when A is oxygen, sulfur or selenium. $R_2$ is hydrogen, halogen, alkyl, alkyl alcohol, alcohol, alkyl thiol, alkyl acid, alkyl amine, amine, aryl, a targeting moiety, carbonyl oxygen, phosphonyl oxygen, or —$OR_5$ when A is boron. $R_3$ is hydrogen, halogen, alkyl, alkyl alcohol, alcohol, alkyl thiol, alkyl acid, alkyl amine, amine, aryl, a targeting moiety, —$OR_5$ when A is boron or phosphorus, or is absent when $R_2$ is carbonyl oxygen. $R_4$, $R_5$, $R_6$, $R_7$ and $R_8$ are each independently hydrogen, halogen, alkyl, alkyl alcohol, alcohol, alkyl thiol, alkyl acid, alkyl amine, amine, aryl, or a targeting moiety. In addition, $R_6$ and $R_7$ may together form a cycloalkyl or aryl structure as is more fully described below.

Suitable transition metal ions prefer sulfur atoms as coordination atoms, and are selected from the group consisting of copper (including Cu+2 or Cu(II)), nickel (including Ni+2 or Ni(II)), palladium (including Pd+2 or Pd(II)) and platinum (including Pt+2 or Pt(II)), with silver (Ag) and gold (Au) being possible in some embodiments as described herein. In most embodiments described herein, the complexes are designed to accept metals in the +2 oxidation state. If silver or gold are used, the ligands and counter-ions may be adjusted, as is known in the art. Generally, Cu, Ni, Pd, and Pt are preferred, with Cu being the most preferred in most embodiments, unless noted.

The choice of A, E, X and M will depend on a variety of factors. Since, in a preferred embodiment, the metal complexes of the invention are neutral, i.e. uncharged, the collective charge of the A, E, X and M moieties preferably equal zero. Thus, as is depicted herein, the choice of A and E will determine whether X is a counter-ion or a ligand. Thus, when A and E are such that they both carry a negative charge (for example when A is oxygen and $R_1$ is absent, and E is sulfur, oxygen, or selenium, with $R_8$ being absent) then X is a neutral ligand. Alternatively, when one or the other of A and E is negatively charged, and the other is neutral, X is a counter-ion. As will be appreciated by those in the art, either A or E should carry a negative charge. Thus, preferred embodiments utilize both A and E with negative charges; A as nitrogen (with $R_1$ present) and E as oxygen, sulfur or selenium, with $R_8$ being absent; or A as oxygen ($R_1$ absent) and E as oxygen or nitrogen with $R_8$ present.

Suitable counter-ions include, but are not limited to, halogens; —OR; —SR; and —NHR, where R is a substituent group as herein defined, preferably alkyl and aryl. By "halogen" herein is meant F, Cl, Br, and I.

By "neutral coordinating ligand" herein is meant a neutral molecule capable of donating electrons to a metal to form a metal-ligand complex without a formal change in oxidation state. Suitable neutral coordinating ligands include, but are not limited to, water ($H_2O$), dioxane, THF, ether (ROR), thioether (RSR), amine ($NR_3$) and phosphine ($PR_3$), with R being any number of groups but preferably an alkyl group.

By "alkyl" herein is meant a straight or branched chain alkyl group, with straight chain alkyl groups being preferred. If branched, it may be branched at one or more positions, and unless specified, at any position. Also included within the definition of an alkyl group are cycloalkyl groups such as saturated and unsaturated C5 and C6 rings. Cycloalkyl also includes heterocycloalkyl, where the heteroatom is oxygen, nitrogen or sulfur. In some cases, two adjacent R groups may together form a ring, i.e. be part of a ring structure, that is, they may be linked to form a cyclic alkyl structure, which may be saturated or unsaturated, or form an aryl, defined below.

The alkyl group may range from about 1 to 20 carbon atoms (C1–C20), with a preferred embodiment utilizing from about 1 to about 10 carbon atoms (C1–C10), with about C1 through about C5 being preferred. However, in some embodiments, the alkyl group may be larger, particularly if it is a straight chain alkyl. Particularly preferred is methyl and propyl. In some cases, alkyl may be heteroalkyl.

By "aryl" or "aryl group" herein is meant aromatic rings including phenyl, benzyl, and naphthyl, heterocyclic aromatic rings such as pyridine, furan, thiophene, pyrrole, indole and purine, and heterocyclic rings with nitrogen, oxygen, sulfur or phosphorus. Preferred aryl groups are phenyl.

The alkyl and aryl groups may be substituted, for example, a phenyl group may be a substituted phenyl group. Suitable substitution groups, generally depicted herein as "R", include, but are not limited to, alkyl and aryl groups, halogens such as chlorine, bromine and fluorine, amines, alcohols, carboxylic acids, and nitro groups; in some cases, as is described herein, the R substitution group may be a targeting moiety. In some embodiments, the targeting moiety may be attached as a substituent group.

By "alkyl acid" or "organic acid" or grammatical equivalents herein is meant an alkyl group containing one or more carboxyl groups, —COOH, i.e. a carboxylic acid. As defined above, the alkyl group may be substituted or unsubstituted. C1–C20 alkyl groups may be used with at least one carboxyl group attached to any one of the alkyl carbons, with C1–C5 being preferred. In a preferred embodiment, the carboxyl group is attached to the terminal carbon of the alkyl group. Other preferred acids include phosphonates and sulfonates.

By "alcohol" herein is meant an —OH group. By "alkyl alcohol" herein is meant an alkyl group containing one or more alcohol groups, similar to the alkyl acids. As defined above, the alkyl group may be substituted or unsubstituted. The alkyl alcohol may be primary, secondary or tertiary, depending on the alkyl group. In a preferred embodiment, the alkyl alcohol is a straight chain primary alkyl alcohol, generally containing at least 2 carbon atoms. Preferred alkyl alcohols include, but are not limited to, ethanol, n-propyl alcohol, n-butyl alcohol, n-pentyl alcohol, n-heptyl alcohol, or n-octyl alcohol. As for the alkyl acids, preferred alkyl alcohols have an alcohol group attached to the terminal carbon of the alkyl group.

By "alkyl thiol" herein is meant an alkyl group containing a thiol (—SH) group at any position, with terminal positions preferred as for acids and alcohols.

By "carbonyl oxygen" herein is meant an oxygen double bonded to a carbon atom. By "phosphonyl oxygen" herein is meant an oxygen double bonded to a phosphorus atom.

By the term "amine" herein is meant an —NRR' group. In this embodiment, R and R' may be the same or different, and may be hydrogen, alkyl or aryl. A preferred —NRR' group is —$NH_2$.

By the term "alkyl amine group" herein is meant an alkyl group, as defined above, with a —NRR' group, as defined above. As defined above, the alkyl group may be substituted or unsubstituted.

In a preferred embodiment, at least one of the R groups of any of the structures depicted herein is a targeting moiety. It is preferred that only one of the R groups be a targeting moiety. In an alternative embodiment, more than one of the R groups may be a targeting moiety.

By the term "targeting moiety" herein is meant a functional group that will specifically interact with the target protein, and thus is used to target the metal complex to a particular target protein. That is, the metal complex is covalently linked to a targeting moiety that will specifically bind or associate with a target protein. For example, the metal complexes of the invention may include a polypeptide inhibitor that is known to inhibit a protease, thus effectively increasing the local concentration of the metal complex at a functional site on the target protein. Suitable targeting moieties include, but are not limited to, polypeptides, nucleic acids, carbohydrates, lipids, hormones including proteinaceous and steroid hormones, growth factors, receptor ligands, antigens and antibodies, and the like, with polypeptides and nucleic acids being preferred.

In a preferred embodiment, the metal complex containing a targeting moiety as one of the R groups inhibits a protein, which may or may not be an enzyme. By "inhibition of a protein" herein is meant that a biological activity of the protein is decreased or eliminated upon binding of the inhibitor. In the case of enzymes, inhibition results in a decrease or loss of enzymatic activity. For example, polypeptides comprising protease substrates or inhibitors are used as an R group on the metal complexes, to form metal complexes that will selectively inhibit the protease. Similarly, a metal complex containing an R group comprising a nucleic acid that specifically binds to a particular nucleic acid binding protein such as a transcription factor is used to selectively inhibit the transcription factor. These targeted metal complexes preferentially bind to the target site on the protein, favoring that site over non-specific binding to other sites or other proteins. This makes the resulting compound more effective at lower concentrations since fewer molecules interact at other sites and minimizes the side-effects due to inhibition of other proteins. Secondary interactions also increase the time spent at the target, giving more opportunity for ligand exchange.

In designing a metal complex for a particular protein, it is to be understood that the high affinity of the metal complex for a sulfur atom of cysteine or the other possible reactive moieties, is such that the metal complex need not be a perfect fit in the active site. Rather, what is important is that the metal complex be able to approach the target axial ligand moiety. For targeting active site residues of enzymes, for example, the metal complexes should generally not be larger than typical enzyme substrates or inhibitors. The gross structure and surface properties of the metal complex will determine its outer sphere interaction with the desired biological active site. Specificity in outer sphere interactions is optimized by variations in size, charge, flexibility, stereochemistry, and surface properties of themetal complex. Thus, in designing an appropriate inhibitor, the characteristics of the protein or enzyme target are exploited.

By the term "polypeptide" herein is meant a compound ranging from about 2 to about 20 amino acid residues covalently linked by peptide bonds. Preferred embodiments utilize polypeptides from about 2 to about 8 amino acids, with about 4 to about 6 being the most preferred. Preferably, the amino acids are naturally occurring amino acids in the L-configuration, although amino acid analogs are also useful, as outlined below. Under certain circumstances, the polypeptide may be only a single amino acid residue. Additionally, in some embodiments, the polypeptide may be larger, and may even be a protein, although this is not preferred. In one embodiment, the polypeptide is glycosylated.

Also included within the definition of polypeptide are peptidomimetic structures or amino acid analogs. Thus, for example, non-naturally occurring side chains or linkages may be used, for example to prevent or retard in vivo degradations. Alternatively, the amino acid side chains may be in the (R) or D-configuration. Additionally, the amino acids, normally linked via a peptide bond or linkage, i.e. a peptidic carbamoyl group, i.e. —CONH—, may be linked via peptidomimetic bonds. These peptidomimetic bonds include $CH_2$—NH—, CO—$CH_2$, azapeptide and retroinversion bonds.

As used herein, "nucleic acid" may refer to either DNA or RNA, or molecules which contain both deoxy- and ribonucleotides. Generally, the nucleic acid is an oligonucleotide, ranging from about 3 nucleotides to about 50 nucleotides, with from about 12 to about 36 being particularly preferred, and at least 21 nucleotides being especially preferred. When the nucleic acid is used solely to confer solubility, the nucleic acid may be smaller, and in some embodiments may be a single nucleotide. The nucleotides may be naturally occurring nucleotides, or synthetic nucleotides, and may be any combination of natural and synthetic nucleotides, although uracil, adenine, thymine, cytosine, guanine, and inosine are preferred. As is more fully described below, the nucleic acids include genomic DNA, cDNA and oligonucleotides including sense and anti-sense nucleic acids. The nucleic acid may be double stranded, single stranded, or contain portions of both double stranded or single stranded sequence. In a preferred embodiment, for example when the nucleic acid is used to target a zinc finger transcription factor, the nucleic acid is double stranded, as zinc fingers bind to the major groove of double stranded nucleic acids. A nucleic acid will generally contain phosphodiester bonds, although in some cases, as outlined below, a nucleic acid may have an analogous backbone, comprising, for example, phosphoramide (Beaucage et al., Tetrahedron 49(10):1925 (1993) and references therein; Letsinger, J. Org. Chem. 35:3800 (1970); Sprinzl et al., Eur. J. Biochem. 81:579 (1977); Letsinger et al., Nucl. Acids Res. 14:3487 (1986); Sawai et al, Chem. Lett. 805 (1984), Letsinger et al., J. Am. Chem. Soc. 110:4470 (1988); and Pauwels et al., Chemica Scripta 26:141 91986)), phosphorothioate, phosphorodithioate, O-methylphosphoroamidite linkages (see Eckstein, Oligonucleotides and Analogues: A Practical Approach, Oxford University Press), or peptide nucleic acid linkages (see Egholm, J. Am. Chem. Soc. 114:1895 (1992); Meier et al., Chem. Int. Ed. Engl. 31:1008 (1992); Nielsen, Nature, 365:566 (1993)). These modifications of the ribose phosphate backbone may be done to facilitate the addition of metal complexes or to increase the stability and half-life of such molecules in physiological environments.

By "carbohydrate" herein is meant a compound with the general formula $C_x(H_2O)_y$. Monosaccharides, disaccharides, and oligo- or polysaccharides are all included within the definition and comprise polymers of various sugar molecules linked via glycosidic linkages. Particularly preferred carbohydrates are those that comprise all or part of the carbohydrate component of glycosylated proteins, including monomers and oligomers of galactose, mannose, fucose, galactosamine, (particularly N-acetylglucosamine), glucosamine, glucose and sialic acid, and in particular the glycosylation component that allows binding to certain receptors such as cell surface receptors. Other carbohydrates comprise monomers and polymers of glucose, ribose, lactose, raffinose, fructose, and other biologically significant carbohydrates.

"Lipid" as used herein includes fats, fatty oils, waxes, phospholipids, glycolipids, terpenes, fatty acids, and glycerides, particularly the triglycerides. Also included within the definition of lipids are the eicosanoids, steroids and sterols, some of which are also hormones, such as prostaglandins, opiates, and cholesterol. Hormones include both steroid hormones and proteinaceous hormones, including, but not limited to, epinephrine, thyroxine, oxytocin, insulin, thyroid-stimulating hormone, calcitonin, chorionic gonadotropin, cortictropin, follicle-stimulating hormone, glucagon, leuteinizing hormone, lipotropin, melanocyte-stimutating hormone, norepinephrine, parathryroid hormone, vasopressin, enkephalins, seratonin, estradiol, progesterone, testosterone, cortisone, and glucocorticoids. Receptor ligands include ligands that bind to receptors such as cell surface receptors, which include hormones, lipids, proteins, glycoproteins, signal transducers, growth factors, cytokines, and others.

In a preferred embodiment, the targeting moiety is a polypeptide. In this embodiment, the polypeptide is chosen on the basis of the target protein or enzyme to be inhibited.

For example, when the target enzyme is a protease, the polypeptide will mimic or comprise an enzyme substrate or the reactive site of an inhibitor. When the polypeptide comprises an inhibitor, the inhibitor may be either a reversible or irreversible inhibitor. The sequence of the polypeptide is chosen to allow the binding of the polypeptide to the active site of the protease.

The polypeptide and the site of attachment of the polypeptide to the metal complex, will be chosen to maximize the interaction of the metal with the active site cysteine. That is, as is explained below, the polypeptide may be attached to the metal complex at the N-terminal or C-terminal end.

As is well known in the art, the active site cysteine of many enzymes is close to the S1–S1' position of the enzyme's substrate (or inhibitor) binding site. Thus, in a preferred embodiment, the polypeptide is chosen to allow optimum interaction of the metal complex with the active site cysteine. For example, the polypeptide may comprise roughly the P4 through P1 residues of a substrate or inhibitor (which occupy the S4 to S1 positions of the enzyme's binding site), and be attached at the C-terminal end (P1) to the metal complex, to maximize the steric interaction of the metal complex with the active site of the enzyme, and particularly the active site cysteine. Alternatively, the polypeptide may comprise the P1' through P4' residues (corresponding to the S1' to S4' positions), with attachment at the N-terminus (P1'). These types of attachments are described below. However, as noted above, the interaction need not be perfect to allow inhibition, since it appears that increasing the local concentration of the metal complex near the active site is sufficient.

Thus, the present invention allows a known enzymatic substrate to be used as an inhibitor, as well as increasing the efficiency of known inhibitors, for example via decreasing the $K_1$. A wide variety of enzyme substrates and inhibitors for a variety of proteases containing either an active site cysteine or an essential metal ion coordinated by a cysteine are known in the art. In addition, the morphological properties of enzymes for which the crystal structures are known are used to design appropriate metal complexes. Alternative embodiments utilize known characteristics about surface charge and hydrophobicity, and substrate and inhibitor specificity.

In a preferred embodiment, the $K_1$ of the polypeptide inhibitor is decreased as a result of attachment to the metal complex. That is, the inhibitor becomes a better inhibitor as a result of the attachment of the metal complex. Thus, the metal complex is effective at lower concentrations since fewer molecules are wasted at other sites.

In a preferred embodiment, at least one of the R groups is a nucleic acid used to target the metal complex to a particular protein or enzyme. For example, the target protein can be a nucleic acid binding protein that has at least one cysteine that is important in biological activity, such as a zinc finger protein.

As is known for zinc finger proteins that bind nucleic acids, it appears that each zinc finger interacts or binds to three base pairs of nucleic acid (see Berg, supra). Thus, the actual sequence of the nucleic acid used to target a nucleic acid binding protein will vary depending on the target protein. Nucleic acid sequences and their target binding proteins are known in the art.

As with the polypeptides, the metal complex can be attached to the nucleic acid in a variety of ways in a variety of positions; the actual methods are described below. The attachment site is chosen to maximize the interaction of a reactive amino acid such as cysteine that is essential for metal ion binding (or an active site cysteine) with the metal complex. In a preferred embodiment, the backbone of the nucleic acid is modified to contain a functional group that can be used for attachment to the metal complex. This functional group may be added to either the 5' or 3' end of the nucleic acid for example. For example, the nucleic acid may be synthesized to contain amino-modified nucleotides using techniques well known in the art (see for example Imazawa et al., J. Org. Chem. 44:2039–2041 (1979); Miller et al., Nucleosides, Nucleotides 12:785–792 (1993); and WO95/15971, and references cited therein). In this embodiment, amine groups are added to the ribophosphate backbone at the 2' or 3' position, thus allowing the attachment of the nucleic acid to the metal complex at either the 5' or 3' end. These amine groups are then used to couple the nucleic acid to the metal complex. Alternatively, nucleotide dimers, containing phosphoramide, phosphorothioate, phosphorodithioate, or O-methylphosphoroamidite linkages may be made, and added to the nucleic acid at any position during synthesis, and the nitrogen or sulfur atom used for attachment using well known techniques, as outlined below. Additionally, the phosphorus atom of the backbone may be used, or linkers, as is known in the art (see for example Thuong et al., Angew. Chem. Intl. Ed. Engl. 32:666–690 (1993); and Mergny et al., Nucleic Acid Res. 22:920–928 (1994)).

Preferred embodiments of Structure 1 are shown below in Structures 2 to 6 and in the Examples:

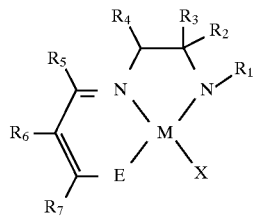

Structure 2

In Structure 2, E is oxygen, sulfur or selenium, $R_3$ is hydrogen; and X is a counter-ion.

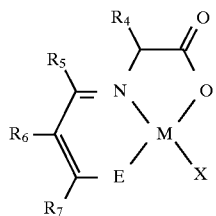

Structure 3

In Structure 3, E is oxygen, sulfur, or selenium and X is a neutral coordinating ligand.

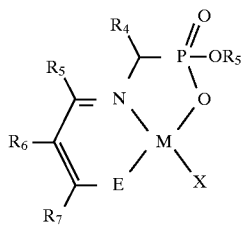

Structure 4

In Structure 4, E is oxygen, sulfur, or selenium, and X is a neutral coordinating ligand.

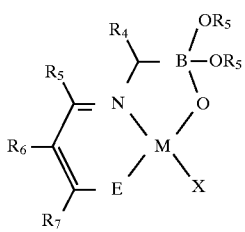

Structure 5

In Structure 5, E is oxygen, sulfur, or selenium and X is a neutral coordinating ligand.

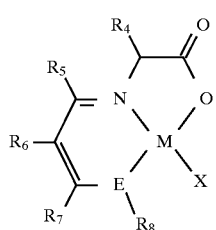

Structure 6

In Structure 6, E is nitrogen, oxygen or sulfur, and X is a counter-ion.

In a preferred embodiment, the metal complexes of the invention have the formula depicted below in Structure 7:

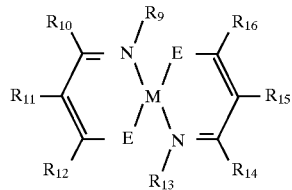

Structure 7

In Structure 7, M is a transition metal ion selected from the group consisting of Cu, Ag, Au, Ni, Pd and Pt, and E is oxygen, sulfur, or selenium, with oxygen being preferred. $R_9$, $R_{10}$, $R_{13}$, and $R_{14}$ are independently hydrogen, halogen, alkyl, alkyl alcohol, alcohol, alkyl thiol, alkyl acid, alkyl amine, amine, aryl, or a targeting moiety. $R_{11}$ and $R_{12}$ are independently hydrogen, halogen, alkyl, alkyl alcohol, alcohol, alkyl thiol, alkyl acid, alkyl amine, amine, aryl, a targeting moiety, or, together may form a cycloalkyl or aryl group. Similarly, $R_{15}$ and $R_{16}$ are independently hydrogen, halogen, alkyl, alkyl alcohol, alcohol, alkyl thiol, alkyl acid, alkyl amine, amine, aryl, a targeting moiety, or, together may form a cycloalkyl or aryl group.

In a preferred embodiment, the metal complexes of the invention have the formula depicted below in Structure 8:

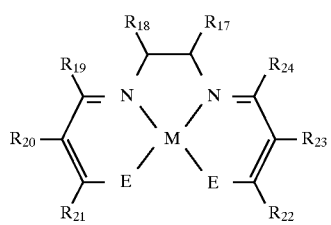

Structure 8

In Structure 8, M is a transition metal ion selected from the group consisting of Cu, Ag, Au, Ni, Pd and Pt, with Cu+2 and Ni+2 being preferred. E is oxygen, sulfur, or selenium, with oxygen being preferred. $R_{17}$, $R_{18}$, $R_{19}$, and $R_{24}$ independently hydrogen, halogen, alkyl, alkyl alcohol, alcohol, alkyl thiol, alkyl acid, alkyl amine, amine, aryl, or a targeting moiety. It should also be understood that there may be two R groups at the $R_{17}$ and $R_{18}$ positions, $R_{17}$ and $R_{17}'$ and $R_{18}$ and $R_{18}'$; preferably these are all hydrogen. $R_{20}$ and $R_{21}$ are independently hydrogen, halogen, alkyl, alkyl alcohol, alcohol, alkyl thiol, alkyl acid, alkyl amine, amine, aryl, a targeting moiety, or together may form a cycloalkyl or aryl group. $R_{22}$ and $R_{23}$ are independently hydrogen, halogen, alkyl, alkyl alcohol, alcohol, alkyl thiol, alkyl acid, alkyl amine, amine, aryl, a targeting moiety, or together may form a cycloalkyl or aryl group.

In a preferred embodiment, the metal complexes of the invention have the formula depicted below in Structure 9:

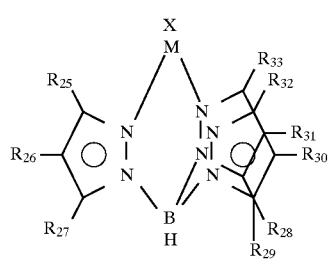

Structure 9

In Structure 9, M is a transition metal ion with an oxidation state of +1, preferably Cu(+1), Au(+1), or Ag(+1). X is a counter-ion. $R_{25}$, $R_{26}$, $R_{27}$, $R_{28}$, $R_{29}$, $R_{30}$, $R_{31}$, $R_{32}$ and $R_{33}$ are independently hydrogen, halogen, alkyl, alkyl alcohol, alcohol, alkyl thiol, alkyl acid, alkyl amine, amine, aryl, a targeting moiety, or, together with an adjacent R group forms a cycloalkyl or aryl group.

In a preferred embodiment, the metal complexes of the invention have the formula depicted below in Structure 10:

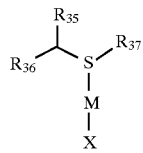

Structure 10

In Structure 10, M is a transition metal ion selected from the group consisting of Cu, Ag, Au, Ni, Pd and Pt, with Au+2 being preferred. X is a counter-ion. $R_{35}$, $R_{36}$ and $R_{37}$ are independently hydrogen, halogen, alkyl, alkyl alcohol, alcohol, alkyl thiol, alkyl acid, alkyl amine, amine, aryl, a targeting moiety, or, together with an adjacent R group forms a cycloalkyl (preferably heterocycloalkyl, with the heteroatom being nitrogen, oxygen, or sulfur) substituted cycloalkyl, aryl, or substituted aryl groups. In a preferred embodiment, at least one $R_{35}$, $R_{36}$, $R_{37}$ or the R substituents of the cycloalkyl or aryl group is a targeting moiety, with polypeptides and nucleic acids being preferred. Thus, preferred embodiments include the structures depicted below:

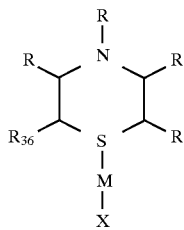

Structure 11

In Structure 11, the R group on the nitrogen atom may be an R group as defined herein or it may be hydrogen.

In a preferred embodiment, the metal complexes of the invention have the formula depicted below in Structure 12:

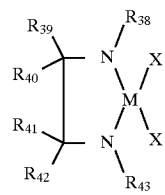

Structure 12

In Structure 12, M is a transition metal ion selected from the group consisting of Cu, Ag, Au, Ni, Pd and Pt. with Cu, Ni, Pd and Pt being preferred. X is a counter-ion. $R_{38}$, $R_{39}$, $R_{40}$, $R_{41}$, $R_{42}$ and $R_{43}$ are independently hydrogen, halogen, alkyl, alkyl alcohol, alcohol, alkyl thiol, alkyl acid, alkyl amine, amine, aryl, or a targeting moiety. In a preferred embodiment, at least one of $R_{38}$ to $R_{43}$ is a targeting moiety.

In a preferred embodiment, the metal complexes of the invention have the formula depicted below in Structure 13:

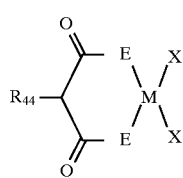

Structure 13

In Structure 13, M is a transition metal ion selected from the group consisting of Cu, Ag, Au, Ni, Pd and Pt, with Cu, Ni, Pd and Pt being preferred. E is oxygen, sulfur or selenium, with oxygen being preferred. Each X is independently a counter-ion. $R_{44}$ is hydrogen, halogen, alkyl, alkyl alcohol, alcohol, alkyl thiol, alkyl acid, alkyl amine, amine, aryl, or a targeting moiety. In a preferred embodiment, at least one of $R_3$ to $R_{43}$ is a targeting moiety.

In one embodiment, the metal complexes of the present invention are labelled. By a "labelled metal complex" herein is meant a metal complex that has at least one element, isotope or chemical compound attached to enable the detection of the metal complex or the metal complex irreversible bound to a protein or enzyme, for example, in assays. In general, labels fall into three classes: a) isotopic labels, which may be radioactive or heavy isotopes; b) immune labels, which may be antibodies or antigens; and c) colored or fluorescent dyes. The labels may be incorporated into the metal complex at any position, for example, as a substituent group. Examples of useful labels include 14C, 3H, biotin, and fluorescent labels as are well known in the art.

The metal complexes of the invention are generally synthesized and purified as necessary as is known in the art and outlined in the Examples.

Once made, the metal complexes of the invention are useful in a wide variety of applications, as is generally outlined herein. In one embodiment, the metal complexes of the invention are useful as general bacteriostatic or bactericidal agents, antimicrobial agents and/or antiviral agents, for both topical and other therapeutic applications. For example, topical antimicrobial agents may be useful in cleaning and disinfectant compositions, as will be appreciated in the art. Therapeutic uses of antimicrobial and antiviral agents are also well known.

The compounds are assayed for antiviral, antimicrobial and antibacterial activity using techniques well known in the art; for example, bactericidal activity may be measured using the techniques outlined in example VI of U.S. Pat. No. 5,049,557. Both in vitro and in vivo antiviral activity may be measured using the techniques outlined in U.S. Pat. No. 5,210,096.

The metal complexes of the invention can also be used to label proteins. Upon incubation of a metal complex of the invention with a protein, certain moieties on the protein will become ligands, resulting in a tightly bound protein-metal complex composition. The preferred ligand from a protein is the sulfur atom of the side chain of cysteine. Thus, a protein with one or more cysteine residues either at the surface of the protein or otherwise accessible to the solvent can be labeled using the metal complexes of the invention.

In this embodiment, the metal complexes of the invention are added or contacted with the target protein. The excess metal complex may be separated, and the labeled protein, with the attached metal complex, is detected as is known in the art.

The stoichiometry of the bound metal complex to protein will vary depending on the number of potential ligands in or at the active site or on the surface of the protein, and may be determined spectrophotometrically, as is understood in the art. Thus, for example, a protein which has four accessible cysteines will generally bind four metal complexes, etc.

Thus, the metal complexes of the present invention are also useful in probing the surface characteristics of a protein.

When used to bind or label proteins, the metal complexes can be coupled, using standard technology, to affinity chromatography columns. These columns may then be used to separate proteins from a sample. For example, depending on the specificity of the metal complex, proteins may be removed from a sample, or specific proteins, such as those containing cysteines at or near the active site may be separated from other components of the sample.

In a preferred embodiment, the metal complexes are useful as enzyme inhibitors. The mechanism of inactivation is similar to the mechanism of protein labeling. In this embodiment, an enzyme has one or more moieties capable of binding as a ligand in the metal complexes of the invention. One or more of such moieties are also functionally important for enzymatic activity, and are inactivated upon contact with the metal complexes of the invention.

For example, enzymes which have cysteine as an active site catalytic residue or have cysteines which are functionally important for enzymatic activity are particularly preferred. Enzymes such as the cysteine proteases outlined herein all have active site cysteines and thus may be inhibited with the compounds of the present invention.

In this embodiment, a metal complex is contacted with the target enzyme. The sulfur atom of the cysteine side chain of an active site cysteine binds to the metal complex as a ligand.

The binding results in the inhibition of the enzyme. The exact mechanism of the inactivation is unknown; however, several possibilities exist. The bound metal complex may sterically interfere with catalytic activity, i.e. it may be bound in or near the catalytic active site. Alternatively, the bound metal complex may interfere with the catalytic mechanism, i.e. by binding to a catalytic cysteine. Additionally, it is also possible that a functionally important moiety at the active site is reduced by the metal ion, and thus the enzyme is inactivated.

In a preferred embodiment, the inactivation of the enzyme by the metal complex inhibitor is effectively irreversible.

In an additional embodiment, metalloproteins are inactivated with the metal complexes of the present invention. Generally, the metals of metalloproteins have ligands such as histidine, cysteine and methionine. If one or more of these residues are inactivated using these metal complexes, the binding of the metal atom may be decreased or eliminated, thus reducing or eliminating biological activity. Particular metalloproteins include, but are not limited to, nucleic acid binding proteins such as "zinc finger" proteins and hemerythrin. Zinc finger proteins utilize histidine and cysteine to bind zinc ions (see Berg, Ann. Rev. Biophys. Biophys. Chem 19:405–421 (1990), Berg, Science 232:485 (1986), and Berg, Prog. Inorg. Chem. 37:143 (1989), hereby expressly incorporated by reference). Zinc finger proteins have been shown to bind nucleic acids and thus play a role in a variety of gene regulatory processes. Zinc finger proteins include transcription factors and other nucleic acid-binding and gene-regulatory proteins (see Berg, Science, supra), and are found in eukaryotes, prokaryotes, and viruses. Other zinc finger proteins suitable for inactivation by the compounds of the present invention include the nucleic acid binding domain of steroid and thyroid hormone receptors and the human oncogene product GLI (see Pavletch et al., Science 261:1701 (1993); Kinzler et al., Nature 332:371 (1988), that contains five zinc finger domains. In a preferred embodiment, one or more of the zinc finger domains utilizes at least one cysteine to bind zinc, with the proteins that utilize two cysteines being preferred. In some cases the metal is bound exclusively by cysteines.

When the metalloprotein is a metalloenzyme, displacement of the active site metal by the metal complex may modulate enzyme activity. Such metalloenzymes include, but are not limited to, the carboxypeptidases, carbonic anhydrase, thermolysin, collagenase, histidinol dehydrogenase, leukotriene A4 hydrolase, adenosine deaminase, superoxide dismutase, alcohol dehydrogenase, lactate dehydrogenase, stromalycin, aminoacyclase, tryptophanyl-tRNA synthetase, and others known in the art.

Testing the efficacy of the metal complexes as inhibitors is routine, as will be appreciated in the art. When the target protein is an enzyme, testing is similar to testing any enzyme inhibitor, as is known in the art. Generally, the enzyme is assayed in the presence and absence of the putative inhibitor, and kinetic parameters are calculated as is known in the art.

The amount of metal complex inhibitor needed to inhibit a given enzyme will vary depending on the number of other reactive axial ligands on the surface of the enzyme, as is outlined above for protein labeling. For example, an enzyme with an active site cysteine and two other "surface" cysteines will generally require at least a 3:1 ratio of metal complex inhibitor:enzyme. The total amount bound to the enzyme may be determined as is known in the art.

Also provided are methods for inhibiting a selected protein or enzyme with the metal complexes of the invention. In this embodiment, the target protein is contacted or exposed to any of the metal complexes described herein. The metal complex can be targetted to a particular protein by the addition of a targeting moiety, such as a polypeptide or a nucleic acid.

Also provided are methods for inhibiting a zinc finger protein, comprising contacting a zinc finger protein with a metal complex. By "inhibiting a zinc finger protein" herein is meant that the biological activity of the zinc finger protein is decreased or eliminated upon exposure to the metal complex. Generally, when the zinc finger protein is a nucleic acid binding protein, this means that the zinc finger will no longer bind the nucleic acid to a significant degree.

In some embodiments, the metal complex is labelled and used for example in a diagnostic assay for the detection or quantification of cysteine proteases in a sample, for example, in blood, lymph, saliva, skin or other tissue samples, in addition to bacterial, fungal, plant, yeast, viral or mammalian cell cultures.

In the preferred embodiment, the metal complexes of the present invention are administered to a patient to treat cysteine protease-associated disorders. By "cysteine protease-associated disorders" or grammatical equivalents herein is meant pathological conditions associated with cysteine proteases. In some disorders, the condition is associated with increased levels of cysteine proteases; for example, arthritis, muscular dystrophy, inflammation, tumor invasion, and glomerulonephritis are all associated with increased levels of cysteine proteases. In other disorders or diseases, the condition is associated with the appearance of an extracellular cysteine protease activity that is not present in normal tissue. In other embodiments, a cysteine protease is associated with the ability of a pathogen, such as a virus, to infect or replicate in the host organism.

Specific examples of cysteine protease associated disorders or conditions include, but are not limited to, arthritis, muscular dystrophy, inflammation, tumor invasion, glomerulonephritis, malaria, Alzheimer's disease, disorders associated with autoimmune system breakdowns, periodontal disease, cancer metastasis, trauma, inflammation, gingivitis, leishmaniasis, filariasis, and other bacterial and parasite-borne infections, and others outlined above.

In particular, disorders associated with interleukin 1β converting enzyme (ICE) are included, as outlined above.

In a preferred embodiment, the enzyme to be inhibited is carbonic anhydrase. Carbonic anhydrase has been implicated in diabetes, ocular disease such as glaucoma, and seizures and convulsions. Accordingly, inhibitors of carbonic anhydrase, such as the metal complexes of the present invention, are useful in the treatment of these conditions.

Thus, in one embodiment, the metal complexes are useful in the treatment of elevated intraocular pressure and glaucoma. Carbonic anhydrase has been implicated in elevated intraocular pressure, and carbonic anhydrase inhibitors have been shown to be efficacious in decreasing this pressure in animals and humans (see Sharir et al., *Experimental Eye Res.* 58(1):107–116 (1994); Rassam et al., *Eye* 7(Pt 5):697–702 (1993); Gunning et al., *Graefes Archive for Clinical and Experimental Ophthalmology* 231(7):384 (1993)).

In an additional embodiment, the metal compounds are useful in the treatment of seizures and convulsions. Carbonic anhydrase II deficient mice have been shown to have increased resistance to chemically induced seizures, and pretreatment with carbonic anhydrase inhibitors has been shown to increase the resistance of normal mice to chemically induced seizures. See Velisek et al., *Epilepsy Res.* 14(2):115–121 (1993).

In a further embodiment, the metal compounds are useful in the treatment of diabetes and abnormal renal function. Elevated levels of carbonic anhydrase have been associated with metabolic diseases like diabetes mellitus and hypertension, and carbonic anhydrase inhibitors have been suggested for treatment. See Parui et al., *Biochem. International* 26(5):809–820 (1992); Parui et al, *Biochem. International* 23(4):779–89 (1991); Dodgson et al., *Arch. Biochem. Biophys.* 277(2):410–4 (1990); Hannedouche et al., *Clinical Sci.* 81(4):457–64 (1991).

In this embodiment, a therapeutically effective dose of a metal complex is administered to a patient. By "therapeutically effective dose" herein is meant a dose that produces the effects for that it is administered. The exact dose will depend on the disorder to be treated and the amount of cysteine protease or other enzyme to be inhibited, and will be ascertainable by one skilled in the art using known techniques. In general, the metal complexes of the present invention are administered at about 1 to about 1000 mg per day. As is known in the art, adjustments for inhibitor degradation, systemic versus localized delivery, and rate of new protease synthesis, as well as the age, body weight, general health, sex, diet, time of administration, drug interaction and the severity of the disease may be necessary, and will be ascertainable with routine experimentation by those skilled in the art.

A "patient" for the purposes of the present invention includes both humans and other animals and organisms. Thus the methods are applicable to both human therapy and veterinary applications. In the preferred embodiment the patient is a mammal, and in the most preferred embodiment the patient is human.

The administration of the metal complexes of the present invention can be done in a variety of ways, including, but not limited to, orally, subcutaneously, intravenously, intranasally, transdermally, intraperitoneally, intramuscularly, intrapulmonary, vaginally, rectally, or intraocularly. In some instances, for example, in the treatment of wounds and inflammation, the metal complexes may be directly applied as a solution or spray.

The pharmaceutical compositions of the present invention comprise a metal complex in a form suitable for administration to a patient. In the preferred embodiment, the pharmaceutical compositions are in a water soluble form. The pharmaceutical compositions may also include one or more of the following: carrier peptides, amino acids and proteins such as serum albumin; buffers; fillers such as microcrystalline cellulose, lactose, corn and other starches; binding agents; sweeteners and other flavoring agents; coloring agents; polyethylene glycol; lipids, and sugars. Additives are well known in the art, and are used in a variety of formulations.

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes. All references cited herein are incorporated by reference.

EXAMPLES

Example 1

Synthesis of metal complexes of Structure 1
Structure 4 complexes
Structure 14

In a 25 ml of ethanol solution, 10 mmoles of salicylaldehyde and 10 mmoles of N-ethylethylene diamine were mixed. The reaction was refluxed for about 1 hour. The reaction cooled to room temperature and ether was added. A oil was recovered after rotoevaporating the sample. The free ligand (about 3 mmoles) which was an oil was then dissolved in warm ethanol and $Cu^{II}Cl_2$ (dissolved in water; 3.5 mmoles) was added. The reaction was refluxed for about an hour and the Cu complex precipitated from solution. It was recrystallized from ethanol.

Structure 14

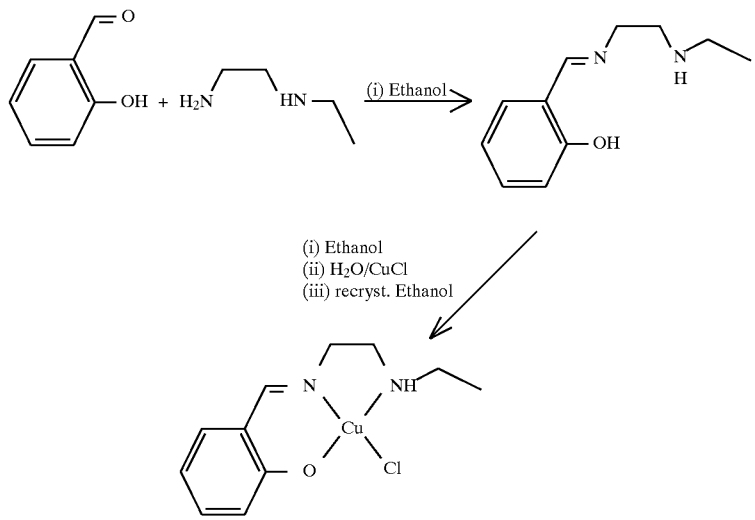

A spectrophotometric assay was used to study papain enzyme activity and inhibition. Two reactions were performed (one with metal complex and without) using 10 μM enzyme, 16 μM of substrate (Ac-Tyr-Val-Ala-Asp-pNA), and 25 μM of metal inhibitor.

Addition of this Structure 14 copper complex at 1 hour resulted in almost complete inhibition of papain. The reaction of the enzyme with the metal compounds was fast (less than 10 minutes). For every molecule of papain there was about 2.5 molecules of copper complex which suggests that a large excess of metal complex is not needed to inhibit the enzyme. Without being bound by theory, the putative reaction between the metal complex at the active site cysteine involves ligand substitution of the Cl for a Cys.

A spectrophotometric assay was used to determine substrate binding and inhibition of Structure 14. The substrate Spectrozyme TH, whose proteolysis releases a chromophore, p-nitroaniline was used. The reaction was carried out with 10 μM thrombin, 16 μM of substrate, and 1 mM metal inhibitor. Only about 10% of the enzyme was inhibited after incubation with the Structure 14 copper complex 1 for one hour. Importantly, the ratio of enzyme to copper complex was about 60,000 to 1. Thus, Structure 14 is more than four orders of magnitude more selective towards a cysteine protease over a serine protease.

The disruption of a zinc finger by the Structure 14 copper complex was shown with Human Sp1 transcription factor using a filter binding assay. 25 ng of Sp1 (Promega) was incubated with 40 fmol of 34P labeled oligonucleotide with and without the metal complex in binding buffer (25 mM Tris, pH=8, 100 mM KCl, 2 mM DTT, 100 uM ZnCl2, and 10% glycerol) at various concentrations of copper inhibitor (0.001 to 0.01 mM). Next the above samples were applied to a nitrocellulose filter (0.45 um Schleicher and Schuell) and wash twiced with buffer (100 mM HEPES, pH=7.5, 1 mM EDTA). The membranes were then incubated in scintillation fluid and then detected by a liquid scintillation counter (Beckman Instruments). Sample treated with the copper complex showed 90% less counts, indicating loss of oligonucleotide bind. Loss of zinc finger function was observed since the metal complex prevented oligonucleotide binding to the zinc finger.

Structure 15

In a 25 ml of ethanol solution, 10 mmoles of salicylaldehyde and 10 mmoles of N-ethylene diamine were mixed. The reaction was refluxed for about 1 hour. The reaction cooled to room temperature and ether was added. A oil was recovered after rotoevaporating the sample. About 3.0 mmoles of free ligand which was an oil was then dissolved in warm ethanol and $Ni^{II}Cl_2$ (dissolved in water; 3.5 mmoles) was added. The reaction was refluxed for about an hour and the Ni complex was recovered as an oil-like material.

Structure 15

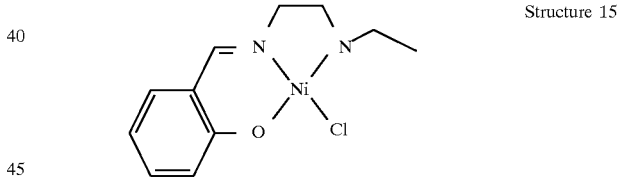

As above, a spectrophotometric assay was used to study papain enzyme activity and inhibition. Once again, two reactions were performed (control and metal complex reaction) using 10 μM enzyme, 16 μM of substrate (Ac-Try-Val-Ala-Asp-pNA), and 25 μM of Structure 15. Inhibition of papain was observed, although with more complex required.

Structure 16

In a 25 ml of ethanol solution, 10 mmoles of both salicylaldehyde and N-ethylethylene diamine were mixed. The reaction was refluxed for about 1 hour. The reaction cooled to room temperature and ether was added. A oil was recovered after rotoevaporating the sample. The free ligand (3.0 mmoles) which was an oil was then dissolved in warm ethanol and $K_2Pt^{II}Cl_6$ (dissolved in water; 3.5 mmoles) was added. The reaction was refluxed for about an hour and the Pt complex precipitated from solution. It was recrystallized from ethanol.

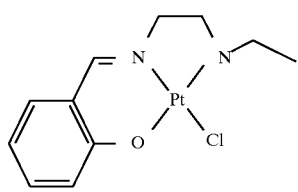

Structure 16

Structure 17

In a 25 ml of ethanol solution, 10 mmoles of both salicylaldehyde and N-phenylethylene diammine were mixed. The reaction was refluxed for about 1 hour. The reaction cooled to room temperature and ether was added. A solid was recovered after rotoevaporating the sample. The free ligand (3 mmoles) was then dissolved in warm ethanol and CuIICl2 (dissolved in water; 3.5 mmoles) was added. The reaction was refluxed for about an hour and the Cu complex precipitated from solution. It was recrystallized from ethanol.

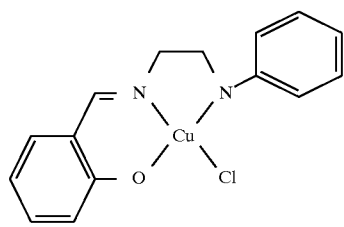

Structure 17

Structure 18

In a 100 ml of ethanol solution, 10 mmoles of both 5-chloro salicylaldehyde and N-ethylethylene diammine were mixed. The reaction was refluxed for about 1 hour. The reaction cooled to room temperature and ether was added. A solid was recovered after rotoevaporating the sample. The free ligand (3 mmoles) was then dissolved in warm ethanol and CuIICl2 (dissolved in water; 3 mmoles) was added. The reaction was refluxed for about an hour and the Cu complex precipitated from solution. It was recrystallized from ethanol.

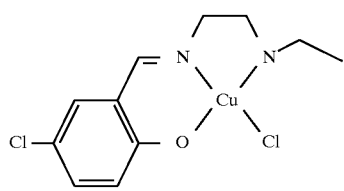

Structure 18

Structure 19

The 5-carboxylic acid salicylaldehyde was first prepared as shown below. The brownish material precipated after the reaction was recrystallized from ethanol to yield 5 grams of the desired product.

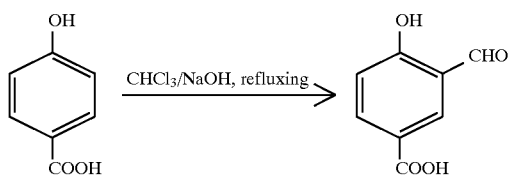

Next, in a 25 ml of ethanol solution, 10 mmoles 5-carboxylic acid salicylaldehyde and 10 mmoles of N-ethylethylene diammine were mixed. The reaction was refluxed for about 1 hour. The reaction cooled to room temperature and ether was added. A solid was recovered after rotoevaporating the sample. The free ligand (3 mmoles) was then dissolved in warm ethanol and CuIICl2 (dissolved in water; 3.5 mmoles) was added. The reaction was refluxed for about an hour and the Cu complex precipitated from solution. It was recrystallized from ethanol.

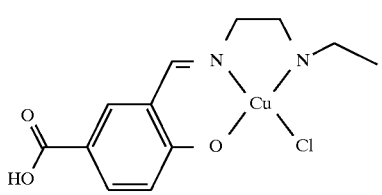

Structure 19

Structure 5
Structure 20

In a 50 ml of ethanol solution, 10 mmoles salicylaldehyde and 10 mmoles of glycine were mixed. The reaction was refluxed for about 1 hour and a solution of CuIICl2 (dissolved in water; 10 mmoles) was added during this time. When the reaction was cooled to room temperature, the product precipitated from solution. It was recrystallized from water.

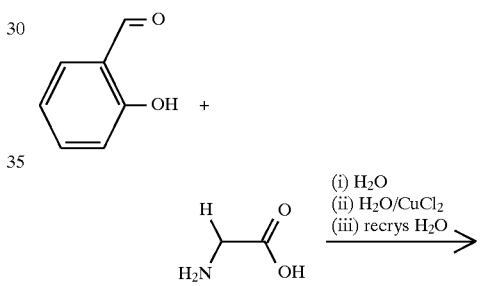

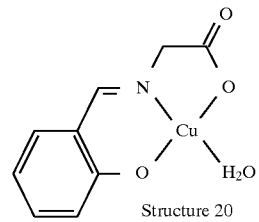

Structure 20

As above, a spectrophotometric assay was used to study papain enzyme activity and inhibition. Once again, two reactions were performed (control and metal complex reaction) using 10 $\mu$M enzyme, 16 $\mu$M of substrate (Ac-Try-Val-Ala-Asp-pNA), and 25 $\mu$M of Structure 15. Inhibition of papain was observed, although with mmolar concentrations required.

Structure 21

In a 50 ml of ethanol solution, 10 mmoles of both salicylaldehyde and tyrosine were mixed. The reaction was refluxed for about 1 hour and a solution of CuIICl2 (dissolved in water; 10 mmoles) was added during this time. When the reaction was cooled to room temperature, the product precipitated from solution. It was recrystallized from water.

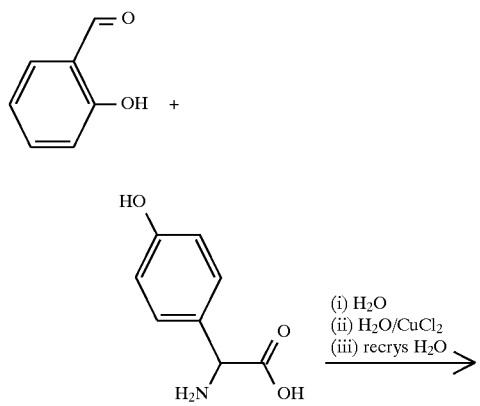

hour and the Cu complex precipitated from solution. It was recrystallized from ethanol.

Structure 23

The 5-carboxylic acid salicylaldehyde is first prepared as shown above. Next the 5-carboxylic acid salicylaldehyde (20 mmoles) is reacted with N-hydroxysuccinimide and DCC in 50 ml of dioxane. The amino acid di pepetide tyr-val (20 mmoles) is then added to the activated carboxylic acid in ethanol. Next, in a 25 ml of ethanol solution, 10 mmoles of both the modified salicylaldehyde and N-ethylethylene diammine are mixed. The reaction is refluxed for about 1 hour. The reaction cools to room temperature and ether is added. A solid is recovered after rotoevaporating the sample. The free ligand is then dissolved in warm ethanol and $Cu^{II}Cl_2$ (dissolved in water; 10 mmoles) is added. The reaction is refluxed for about an hour and the Cu complex precipitates from solution. It is recrystallized from ethanol.

Structure 23

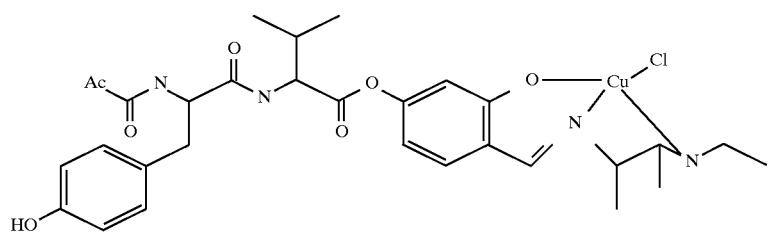

-continued

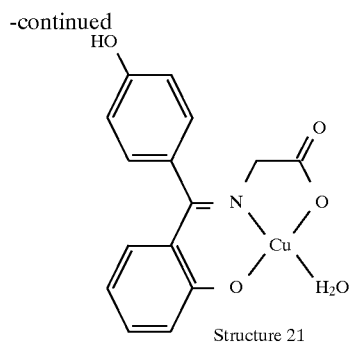

Structure 21

EXAMPLE 2

Synthesis of Structure 1 compounds with targeting moieties

Structure 22

The 5-carboxylic acid salicylaldehyde was first prepared as shown above. Next the 5-carboxylic acid salicylaldehyde (20 mmoles) was reacted with N-hydroxysuccinimide and DCC in 50 ml of dioxane. The amino acid tri pepetide gly-gly-gly (20 mmoles) was then added to the activated carboxylic acid in ethanol. Next, in a 25 ml of ethanol solution, 10 mmoles of both the modified salicylaldehyde and N-ethylethylene diammine were mixed. The reaction was refluxed for about 1. The reaction cooled to room temperature and ether was added. A solid was recovered after rotoevaporating the sample. The free ligand was then dissolved in warm ethanol and CuIICl2 (dissolved in water; 10 mmoles) was added. The reaction was flux for about an

EXAMPLE 3

Synthesis of metal complexes of Structure 7
Structure 24

In a 25 ml of ethanol solution, 10 mmoles of both salicylaldehyde and 3-amino propanol were mixed. The reaction was refluxed for about 1 hour. The reaction cooled to room temperature and oil was recovered. The free ligand (10 mmoles) was then dissolved in warm ethanol and CuIICl2 (dissolved in water; 5 mmoles) was added. The reaction was refluxed for about an hour and the 2:1 Cu complex precipitated from solution. It was recrystallized from ethanol.

Structure 24

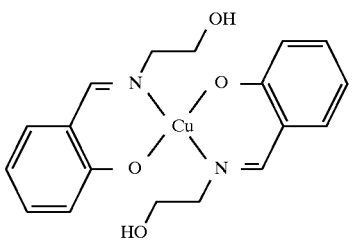

A spectrophotometric assay was used to study papain enzyme activity and inhibition. Once again, two reactions were performed (control and metal complex reaction) using 10 $\mu$M enzyme, 16 $\mu$M of substrate (Ac-Tyr-Val-Ala-Asp-pNA), and 25 $\mu$M of Structure 24. As above, inhibition of papain was observed. This complex is similar in that the complex contains copper, however the coordination spheres is dramatically different. The cysteine must bind in an axial position in this complex, since ligand substitution in the metal plane is not feasible.

EXAMPLE 4

Synthesis of metal complexes of Structure 8

Structure 25

In a 30 ml of ethanol solution, 20 mmoles of salicylaldehyde and 10 mmoles of ethylene diamine were mixed at a 2:1 molar ratio. The reaction was refluxed for about 1 hour. The reaction cooled to room temperature and free ligand precipitated from solution. The free ligand (20 mmoles) was then dissolved in warm ethanol and CuIICl2 (dissolved in water; 20 mmoles) was added. The reaction was refluxed for about an hour and the Cu complex precipitated from solution. It was recrystallized from ethanol.

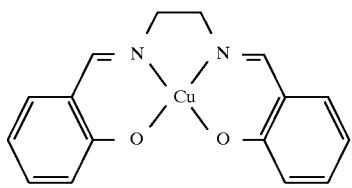

Structure 25

Structure 26

In a 30 ml of ethanol solution, 20 mmoles of salicylaldehyde and 10 mmoles of ethylene diamine were mixed at a 2:1 molar ratio. The reaction was refluxed for about 1 hour. The reaction cooled to room temperature and free ligand precipitated from solution. The free ligand (20 mmoles) was then dissolved in warm ethanol and NiIICl2 (dissolved in water; 20 mmoles) was added. The reaction was refluxed for about an hour and the Ni complex precipitated from solution. It was recrystallized from ethanol.

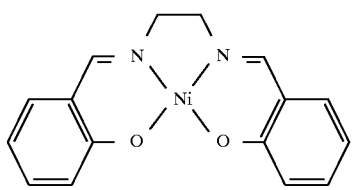

Structure 26

EXAMPLE 5

Synthesis of metal complexes of Structure 9

Structure 26

The free ligand bpz is dissolved in warm ethanol. Copper (I) chloride is then added under argon and the solution is refluxed for an hour. The reaction is cooled in ice and the copper complex precipitates.

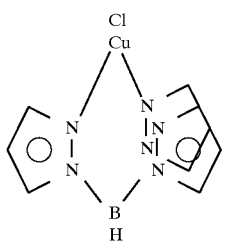

Structure 27

EXAMPLE

Synthesis of a metal complex of Structure 10

Structure 28

A represative example form this class of molecules is described. The 10 mmoles of the amino thioether was dissolved in 20 ml of ethanol. One equivalent of HAuCl4 was then added. The reaction was kept in the dark. The reaction was stirred at room temperature for one hour. The gold complex precipitated from solution as a white powder. Ether can also be added to precipitate the gold thioethers from solution.

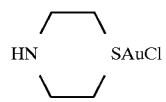

Structure 28

A spectrophotometric assay was used to study papain enzyme activity and inhibition. Once again, two reactions were performed (control and metal complex reaction) using 10 $\mu$M enzyme, 16 $\mu$M of substrate (Ac-Tyr-Val-Ala-Asp-pNA), and 25 $\mu$M of the Structure 28 gold complex. Inhibition of papain was observed immediately upon addition of the metal complex. This suggest that gold complexes can be effective inhibitors of cysteine proteases.

We claim:

1. A metal complex having the formula:

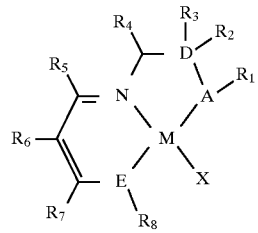

wherein

M is a transition metal ion selected from the group consisting of Cu, Ag, Au, Ni, Pd and Pt;

A is either nitrogen or oxygen;

E is oxygen, sulfur, nitrogen or selenium;

D is carbon, boron or phosphorus;

X is a counterion or a neutral coordinating ligand;

$R_1$ is hydrogen, halogen, alkyl, alkyl alcohol, alcohol, alkyl thiol, alkyl acid, alkyl amine, amine, aryl, a targeting moiety, or may be absent when A is oxygen, sulfur or selenium;

$R_2$ is hydrogen, halogen, alkyl, alkyl alcohol, alcohol, alkyl thiol, alkyl acid, alkyl amine, amine, aryl, a targeting moiety, carbonyl oxygen, phosphonyl oxygen, or —$OR_5$ when A is boron;

$R_3$ is hydrogen, halogen, alkyl, alkyl alcohol, alcohol, alkyl thiol, alkyl acid, alkyl amine, amine, aryl, a targeting moiety, —$OR_5$ when A is boron or phosphorus, or is absent when $R_2$ is carbonyl oxygen;

$R_4$ is hydrogen, halogen, alkyl, alkyl alcohol, alcohol, alkyl thiol, alkyl acid, alkyl amine, amine, aryl, or a targeting moiety;

$R_5$ is hydrogen, halogen, alkyl, alkyl alcohol, alcohol, alkyl thiol, alkyl acid, alkyl amine, amine, aryl, or a targeting moiety;

$R_6$ is hydrogen, halogen, alkyl, alkyl alcohol, alcohol, alkyl thiol, alkyl acid, alkyl amine, amine, aryl, a targeting moiety, or, together with $R_7$, may form a cycloalkyl or aryl group;

$R_7$ is hydrogen, halogen, alkyl, alkyl alcohol, alcohol, alkyl thiol, alkyl acid, alkyl amine, amine, aryl, a targeting moiety, or, together with $R_6$, may form a cycloalkyl or aryl group; and $R_8$ is hydrogen, halogen, alkyl, alkyl alcohol, alcohol, alkyl thiol, alkyl acid, alkyl amine, amine, aryl, a targeting moiety, or may be absent when E is oxygen, sulfur or selenium, wherein at least one of R1 to R8 is a targeting moiety.

2. A metal complex according to claim 1 wherein M is Cu+2.

3. A metal complex according to claim 1 having the formula:

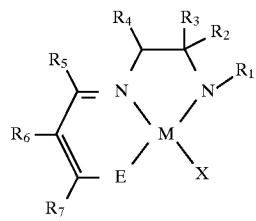

wherein
E is oxygen, sulfur or selenium;
$R_3$ is hydrogen; and
X is a counterion.

4. A metal complex according to claim 1 having the formula:

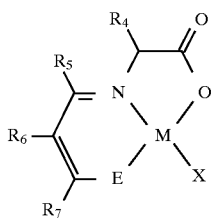

wherein
E is oxygen, sulfur, or selenium; and
X is a neutral coordinating ligand.

5. A metal complex according to claim 1 having the formula:

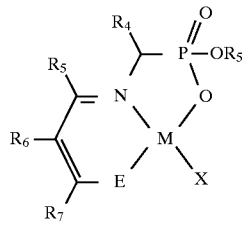

wherein
E is oxygen, sulfur, or selenium; and
X is a neutral coordinating ligand.

6. A metal complex according to claim 1 having the formula:

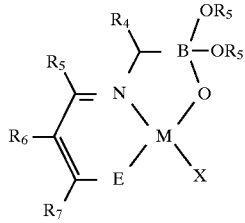

wherein

E is oxygen, sulfur, or selenium; and
X is a neutral coordinating ligand.

7. A metal complex according to claim 1 having the formula:

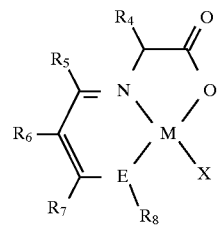

wherein

E is nitrogen, oxygen or sulfur; and
X is a counter-ion.

8. A metal complex having the formula:

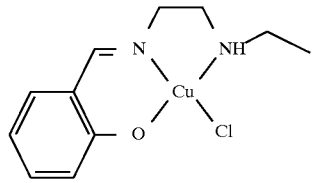

9. A metal complex having the formula:

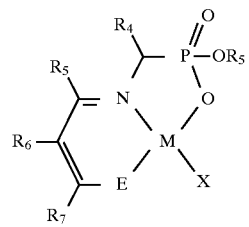

wherein

M is a transition metal ion selected from the group consisting of Cu, Ag, Au, Ni, Pd and Pt;

$R_4$ is hydrogen, halogen, alkyl, alkyl alcohol, alcohol, alkyl thiol, alkyl acid, alkyl amine, amine, aryl, or a targeting moiety;

$R_5$ is hydrogen, halogen, alkyl, alkyl alcohol, alcohol, alkyl thiol, alkyl acid, alkyl amine, amine, aryl, or a targeting moiety;

$R_6$ is hydrogen, halogen, alkyl, alkyl alcohol, alcohol, alkyl thiol, alkyl acid, alkyl amine, amine, aryl, a targeting moiety, or, together with $R_7$, may form a cycloalkyl or aryl group;

$R_7$ is hydrogen, halogen, alkyl, alkyl alcohol, alcohol, alkyl thiol, alkyl acid, alkyl amine, amine, aryl, a targeting moiety, or, together with $R_6$, may form a cycloalkyl or aryl group;

E is oxygen, sulfur, or selenium; and
X is a neutral coordinating ligand.

10. A metal complex having the formula:

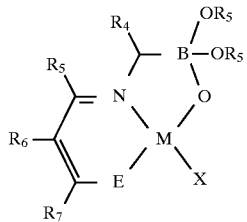

wherein

M is a transition metal ion selected from the group consisting of Cu, Ag, Au, Ni, Pd and Pt;

$R_4$ is hydrogen, halogen, alkyl, alkyl alcohol, alcohol, alkyl thiol, alkyl acid, alkyl amine, amine, aryl, or a targeting moiety;

$R_5$ is hydrogen, halogen, alkyl, alkyl alcohol, alcohol, alkyl thiol, alkyl acid, alkyl amine, amine, aryl, or a targeting moiety;

$R_6$ is hydrogen, halogen, alkyl, alkyl alcohol, alcohol, alkyl thiol, alkyl acid, alkyl amine, amine, aryl, a targeting moiety, or, together with $R_7$, may form a cycloalkyl or aryl group;

$R_7$ is hydrogen, halogen, alkyl, alkyl alcohol, alcohol, alkyl thiol, alkyl acid, alkyl amine, amine, aryl, a targeting moiety, or, together with $R_6$, may form a cycloalkyl or aryl group;

E is oxygen, sulfur, or selenium; and

X is a neutral coordinating ligand.

11. A pharmaceutical composition comprising a metal complex according to claim 1, 2, 4, 5, 6, 7, 8 or 8 in admixture with a pharmaceutically acceptable carrier.

12. A method of inhibiting a cysteine protease comprising irreversibly binding a metal complex according to claim 1, 2, 4, 5, 6, 7, or 8 to said cysteine protease.

13. A method of treating cysteine protease associated-disorders comprising administering to a patient a therapeutically effective dose of a metal complex according to claim 1, 2, 4, 5, 6, 7, or 8.

* * * * *